United States Patent [19]  [11] 4,138,406
Balasfalvy  [45] Feb. 6, 1979

[54] MANUFACTURE OF MALEIMIDES VIA CYCLIZING DEHYDRATION

[75] Inventor: Ferenc Balasfalvy, Basel, Switzerland

[73] Assignee: Ciba-Geigy Corporation, Ardsley, N.Y.

[21] Appl. No.: 761,086

[22] Filed: Jan. 21, 1977

Related U.S. Application Data

[63] Continuation-in-part of Ser. No. 558,984, Mar. 17, 1975, abandoned, which is a continuation-in-part of Ser. No. 524,686, Nov. 18, 1974, abandoned.

[30] Foreign Application Priority Data

Nov. 22, 1973 [CH] Switzerland ................. 16471/73

[51] Int. Cl.$^2$ ............... C07D 207/44; C07D 405/14; C07D 403/14; C07D 403/10
[52] U.S. Cl. ................. 260/326.26; 260/326.5 FM
[58] Field of Search ............... 260/326.26, 326.5 FM

[56] References Cited

U.S. PATENT DOCUMENTS

| | | | |
|---|---|---|---|
| 3,127,414 | 3/1964 | Cole | 260/326.26 |
| 3,522,271 | 7/1970 | Kalil | 260/326.26 |
| 3,627,780 | 12/1971 | Bonnard | 260/326.26 |
| 3,839,358 | 10/1974 | Bargain | 260/326.26 |

OTHER PUBLICATIONS

Naumov et al., Chem. Abs. 75, 87793f (1971).

*Primary Examiner*—Mark L. Berch
*Attorney, Agent, or Firm*—Luther A. R. Hall

[57] ABSTRACT

The invention relates to a process for the manufacture of maleimides by cyclic dehydration of corresponding maleamic acids in the presence of acetic anhydride and a calcium, barium or strontium oxide, acetate or alcoholate (catalyst). Compared to known catalysts, especially nickel salts, these alkaline earth metal compounds used as catalysts according to the invention have the advantage that the manufacturing process gives substantially greater kettle yields, and that the compounds are non-toxic. Preferably, calcium oxide and calcium acetate are employed according to the invention. Corresponding barium compounds are also very suitable for use.

14 Claims, No Drawings

MANUFACTURE OF MALEIMIDES VIA CYCLIZING DEHYDRATION

This is a continuation-in-part of my copending application Ser. No. 558,984 filed Mar. 17, 1975, now abandoned which in turn is a continuation-in-part of my application Ser. No. 524,686 filed Nov. 18, 1974 (now abandoned).

In recent years, maleimides have acquired considerable importance as starting materials for the manufacture of high polymers. They can be polymerised by themselves or in combination with other suitable monomers, by warming or catalytically. A polyaddition reaction of polymaleimides with organic polyamides is also known. Given this importance of the maleimides, it is necessary for the chemical raw materials industry to develop advantageous processes for the manufacture of maleimides.

It is already known to manufacture bis-maleimides by reaction of the corresponding bis-maleamic acids with a lower carboxylic acid anhydride (for example acetic anhydride) in the presence of an organic diluent and of a soluble nickel derivative. Such a process is described, and claimed, in DT-OS 2,040,094. This Offenlegungsschrift refers to U.S. Pat. No. Specifications 2,444,536, 3,018,290, 3,018,292 and 3,127,414 which relate to further known processes for the manufacture of maleimides.

Whilst the process according to DT-OS No. 2,040,094 represents a technical advance compared to the known processes mentioned in the same specification, it still suffers from considerable disadvantages.

Thus, for example, the kettle yield is very low (even in industrial installations). Kettles of capacity approximately 2,000 l must be employed for the production of 70 kg of maleimide. Apart from the fact that the nickel salts used as catalysts are relatively expensive, their use is also very disadvantageous for ecological reasons. Since the effluents contain 100 times as much nickel salts as is permitted at the present time and the removal of these salts from the effluent is extremely costly, the process according to DT-OS 2,040,094 has found virtually no industrial acceptance.

British Pat. No. 1,137,592 describes a multi-stage process for the manufacture of bis-maleimides in which a sodium salt of a carboxylic acid is used as the catalyst both for the manufacture of the bis-maleamic acid and for the cyclising dehydration thereof to the imide. However, this process is disadvantageous inasmuch as the catalyst must be employed in high concentration (that is to say up to 3 mols per mol of the diamine employed), which requires a costly washing operation of the end product to remove the catalyst. Furthermore, the yields obtained in carrying out this known process (82 to 88% of theory) are too low.

Accordingly, it is the object of the invention to discover a process which operates with a better space yield, which presents no problems with regard to the effluents (in respect of amount and toxicity) and which is thus overall substantially more economical in operation than the processes according to the state of the art.

The subject of the invention is a process for the manufacture of monomaleimides or polymaleimides by cyclising dehydration at temperatures between 40° and 100° C. of a member selected from the group consisting of
(a) phenyl maleamic acid,
(b) a polymaleamic acid of the general formula

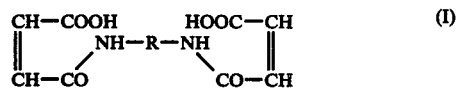

in which R denotes a radical of the formula

wherein $R^1$ represents one of the radicals —$CH_2$—,

—$SO_2$—, —SO—, —S—, —CO— and —O—,
(c) a polymaleamic acid of the formula

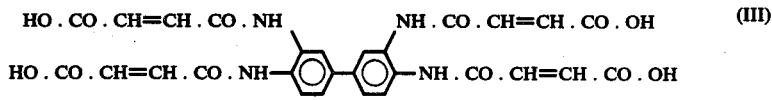

(d) a polymaleamic acid of the formula

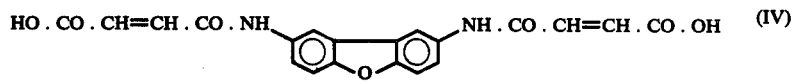

in the presence of acetic anhydride, catalysts, and a member selected of the group consisting of trialkylamines and N,N-dialkylbenzylamines with 1 to 12 C atoms in each alkyl group and in the presence or absence of organic solvents, characterized in that the catalyst employed is a calcium, barium or strontium oxide, acetate or alcoholate in a concentration of 0.005 to 0.2 mol per mol of the monomaleamic or polymaleamic acid.

The preferred range of catalyst concentration is 0.01 to 0.1 mol per mol of the maleamide-carboxylic acid.

Particularly suitable catalysts according to the invention are calcium, barium or strontium oxides and acetates. Calcium compounds and barium compounds are employed preferably. The following substances should be mentioned as examples of the catalysts: calcium acetate, calcium oxide, barium acetate, barium oxide and strontium oxide. Calcium, barium or strontium alcoholates or corresponding complex compounds are also suitable.

Preferably, 2 to 3 mols of acetic anhydride should be used per mol of maleamic acid.

The preferred concentration of the trialkylamines or N,N-dialkylbenzylamines is between 0,3 and 1 mol per mol maleamic acid. Trialkylamines are employed preferably.

The cyclising dehydration is carried out at temperatures between 40° C. and 100° C., preferably at atmospheric pressure. Preferably, it is carried out at temperatures between 40 and 60° C. and in the presence of organic solvents.

Amongst the solvents which can be used there may be mentioned solvents of elevated polarity, such as, for example, dimethylformamide, dimethylacetamide, dimethylsulphoxide, N-methylpyrrolidone and N-methylcaprolactam. It is also possible to use cyclic ethers, such as, for example, tetrahydrofuran.

Preferably N,N'-4,4'-diphenylmethane-bis-maleamic acid and N,N'-4,4'-diphenylsulphone-bis-maleamic acid are used as compounds of the formula I. In addition it is in principle also possible to employ all the bis-maleamic acids which are listed in DT-OS 2,040,094.

The monomaleamic acids and polymaleamic acids used as starting materials for the process according to the invention can be manufactured according to known processes which are described in detail in the abovementioned patent specifications, which quote the relevant literature.

Particularly suitable starting materials for the process according to the invention are, however, monomaleamic acids or polymaleamic acids which have been manufactured by reaction of maleic anhydride with aniline or polyamines in the presence of organic solvents and in the presence of 0.005 to 0.2 mol of a catalyst per mol of the monoamine or polyamine.

In manufacturing these preferred starting materials, maleic anhydride is reacted with the particular monoamine or polyamine in a ratio such that 0.8 to 1.2, preferably 0.95 to 1.1, mols of maleic anhydride are present per equivalent of amine.

If the process according to the invention is carried out in 2 stages in the manner described, yet a further advantage surprisingly results. This is that the maleamic acid produced in the 1st stage proves to be stable to heat and to polymerisation. The consequence of this is that the organic solvent present from the 1st stage can be removed wholly or partially, preferably by distillation, prior to the cyclising dehydration, without producing significant amounts of by-products resulting from degradation or polymerisation. This stabilising effect is particularly marked and the success of the two-stage process of optimal, if, after carrying out the 1st stage of the process, 25 to 50% by weight of the solvent (reactants are not here to be understood as solvents) is removed.

The maleimides which can be manufactured by the process according to the invention are in general obtained in the form of a suspension in the particular organic solvent, and a part of the particular maleimide can also be present in solution. Complete precipitation of the desired end product is then achieved by adding non-solvents such as, for example, water. In most cases, thorough washing (preferably with water) of the maleimide obtained after filtration suffices to give an adequately pure, industrially usable product.

The technical advance achieved by the process according to the invention can be summarised as follows. The kettle yield is, surprisingly, substantially greater than with the process according to DT-OS 2,040,094; kettles of approximate capacity 1,000 l suffice for the production of 70 kg of maleimide. The alkaline earth metal compounds used as the catalyst a priori eliminate the ecological problems. As compared to the use of alkali metal compounds as catalysts according to known processes, the use of the alkaline earth metal compounds according to the invention gives the following advantages. Costly washing operations are not necessary since the concentration required according to the invention is much lower. It is surprising that higher yields (preferably 95-97% of theory) are achieved.

The maleimides manufactured in accordance with the process of the invention are, surprisingly, substantially more active with regard to thermal polymerisation than the products manufactured according to known processes. This behaviour is especially desirable inasmuch as fillers and additives can be added to the reaction mixtures to be polymerised, in order to improve the materials to be manufactured and cheapen them, without thereby making the reactivity too low. This unexpected behaviour of the maleimides manufactured by the process according to the invention, though they have the same analytical data as maleimides manufactured according to known processes, particularly underlines the inventive level of the process claimed.

EXAMPLE 1

30.9 g of maleic anhydride (0.315 mol) and 118.0 g of acetone are initially introduced into a flask equipped with a reflux condenser and the mixture is stirred at 25° C. until complete solution is achieved.

0.2 g of calcium oxide (0.00356 mol) is added to this solution and stirring is continued for 15 minutes. The mixture is warmed to 60° C. and a solution of 29.7 g of 4,4'-diaminodiphenylmethane (0.149 mol) in 59.2 g of acetone is added dropwise at this temperature over the course of approx. 1 hour.

87 g of acetone are distilled from the reaction mixture at a bath temperature of 60° C., whilst stirring and under vacuum (approx. 40-100 mm Hg). A yellow crystal mass results. 2.0 g of glacial acetic acid, 48.6 g of acetic anhydride (0.476 mol) and 5.25 g of triethylamine (0.057 mol) are added to this crystal mass. The reaction mixture is warmed to 60° C. and stirred for 2 hours at this temperature. A brown solution results. This solution is filtered warm (60° C.) through a filter covered with silica powder and the latter is rinsed with 6.0 g of acetone. The solution is cooled to 25° C. 450 ml of water are added dropwise at this temperature over the course of 2-3 hours. A crystal suspension results. This crystal suspension is cooled to 10° C. and stirred at this temperature for 1 hour. It is then filtered and the crystalline residue is rinsed with 150 ml of cold (10° C.) water in portions. The crystals are dried in a vacuum drying cabinet in vacuo at 80° C.

Yield: 48.2 g of N,N'-4,4'-diphenylmethane-bis-maleimide, corresponding to 90.0% of theory relative to 4,4'-diaminodiphenylmethane (theory = 53.5 g), melting point: 152-157° C.

EXAMPLE 2

The procedure followed is exactly as in Example 1 except that instead of 0.2 g of calcium oxide 0.3 g of calcium acetate (0.0019 mol) is employed. The result of this experiment virtually corresponds to the result of Example 1.

EXAMPLE 3

The procedure followed is exactly as in Example 1 except that instead of 0.2 g of calcium oxide 0.2 g of barium oxide (0.00118 mol) is employed. The result corresponds to that of Example 1.

EXAMPLE 4

The procedure followed is exactly as in Example 1, except that instead of 0.2 g of calcium oxide 0.3 g of barium acetate (0.00118 mol) is employed. The result corresponds to that of Example 1.

EXAMPLE 5

48.6 g of acetic anhydride, 5.25 g of triethylamine and 3.0 g of calcium acetate (0.019 mol) are initially introduced into a flask equipped with a reflux condenser.

The mixture is warmed to 60° C. whilst stirring. A solution, warmed to 60° C., of 59.1 g of N,N'-4,4'-diphenylmethane-bis-maleamic acid (0.15 mol) and 144.0 g of dimethylformamide is added dropwise to the above mixture over the course of 1 hour at 60° C. The mixture is stirred for a further ½ hour at 60° C. A viscous solution results.

This solution is allowed to cool to 30° C. and is run over the course of 1 hour into a mixture of 225 g of ice and 225 g of water (maximum temperature during the addition: +10° C.).

After completion of the addition, the crystals are filtered off and rinsed with 200 g of cold (10° C.) water. The crystals are dried in vacuo at 80° C. in a vacuum drying cabinet.

Yield: 51.0 g of N,N'-4,4'-diphenylmethane-bis-maleimide, corresponding to 95.4% of theory, relative to N,N'-4,4'-diphenylmethane-bis-maleamic acid. (Theory = 53.5 g).

Melting point: 156°–159° C.

EXAMPLE 6

28.42 g of maleic anhydride (0.29 mol) and 73 g of dimethylformamide are initially introduced into a flask equipped with a reflux condenser, the mixture is warmed to 60° C. (which produces a solution) and a solution, warmed to 60° C., of 29.7 g of 4,4'-diaminodiphenylmethane (0.15 mol) in 73 g of dimethylformamide is added dropwise to the above solution over the course of 1 hour at 60° C. 5.25 g of triethylamine are added to the reaction mixture. The mixture is then stirred at 60° C. until a solution is produced. The latter is allowed to cool to 40° C. and is added dropwise over the course of 1 hour to a mixture of 48.6 g of acetic anhydride and 3.0 g of calcium acetate (0.019 mol) at 60° C.

The reaction mixture is kept for 1 hour at 60° C., whilst stirring. A viscous solution results. This solution is allowed to cool to 30° C. and is added dropwise over the course of approx. 1 hour to a mixture of 225 g of ice and 225 g of water (with the temperature not exceeding 10° C. during the addition).

After completion of the addition, the crystals are filtered off and rinsed with 200 g of water at 10° C. The crystals are dried in vacuo at 80° C. in a vacuum drying cabinet.

Yield: 50.6 g of N,N'-4,4'-diphenylmethane-bis-maleimide, corresponding to 94.6% of theory, relative to 4,4'-diaminodiphenylmethane. (Theory = 53.5 g). Melting point: 159°–162° C.

EXAMPLE 7

29.7 g of 4,4'-diaminodiphenylmethane (0.15 mol), 59.0 g of acetone and 23.7 g of benzyldimethylamine are initially introduced into a flask equipped with a reflux condenser. The mixture is stirred at 25° C. until a solution results. This solution is cooled to 10°–15° C. A solution of 28.42 g of maleic anhydride (0.29 mol) in 119 g of acetone is added dropwise to the above solution over the course of 1 hour at 10°–15° C. Thereafter, the resulting solution is added dropwise to a mixture of 48.6 g of acetic anhydride and 3.0 g of calcium acetate (0.019 mol) over the course of 1 hour at 60° C. The reaction mixture is warmed to 65°–70° C. 45 g of acetone are then distilled off under normal pressure.

The viscous solution which remains is allowed to cool to 30°–35° C. and is run, over the course of 1 hour, into a mixture of 225 g of ice and 225 g of water. After completion of the addition, the crystals are filtered off and rinsed with 200 g of water at 10° C. The crystals are dried in vacuo at 80° C. in a vacuum drying cabinet.

Yield: 52.0 g of N,N'-4,4'-diphenylmethane-bis-maleimide, corresponding to 97.2% of theory, relative to 4,4'-diaminodiphenylmethane. (Theory = 53.5 g). Melting point: 158°–160° C.

EXAMPLE 8

25.0 g of 3,3',4,4'-biphenyltetramine (0.116 mol) and 72.0 g of dimethylformamide are initially introduced into a flask equipped with a reflux condenser. The mixture is stirred at 25° C. until a solution results. This solution is warmed to 60° C. and a solution of 48.05 g of maleic anhydride (0.49 mol) in 72.0 g of dimethylformamide is added dropwise to the above solution over the course of 1 hour at 60°–65° C. The reaction mixture is kept at 60°–65° C. for 1 hour, whilst stirring. The mixture is cooled to 25° C. and 71.6 g of acetic anhydride (0.701 mol), 2.3 g of calcium acetate (anhydrous; 0.0145 mol) and 5.9 g of triethylamine (0.058 mol) are added in succession. The reaction mixture is warmed to 60°–65° C. and is kept at this temperature for 2 hours, whilst stirring. A solution of medium viscosity results. This is allowed to cool to 30°–35° C. and 900 g of distilled water are run in over the course of one hour. Thereafter, the resulting crystal/liquid mixture is cooled to 0°–5° C. and is kept at this temperature for one hour, whilst stirring. It is then filtered and the crystals are rinsed with 300 g of distilled water at 10° C. The crystals are dried in vacuo at 80° C. in a vacuum drying cabinet.

Yield: 48.8 g of 3,3',4,4'-biphenyltetramaleimide, corresponding to 78.2% of theory, based on 3,3'-4,4'-biphenyltetramine (theory = 62.35 g). Melting point: not characteristic, product does not melt below 250° C. N content (Kjehldal method): 88.95% of the theoretical content free amine (by titration with sodium nitrite): < 0.3%.

EXAMPLE 9

45.0 g of aniline (0.483 mol) and 100.0 g of dimethylformamide are introduced into a flask equipped with a reflux condenser. The mixture is stirred at 25° C. until a solution results. This solution is warmed to 60° C. A solution of 49.7 g of maleic anhydride (0.506 mol) in 74.0 g of dimethylformamide is added dropwise to the above solution over the course of 1 hour at 60°–65° C. The reaction mixture is kept at 60°–65° C. for 1 hour, whilst stirring. It is then cooled to 25° C. and 73.9 g of acetic anhydride (0.723 mol), 9.5 g of calcium acetate (anhydrous; 0.060 mol) and 14.6 g of triethylamine (0.144 mol) are added in succession. The reaction mixture is warmed to 60°–65° C. and kept at this temperature for 2 hours, whilst stirring. A solution of medium viscosity results, which is cooled to 30°-35° C. 1,000.0 g of distilled water are allowed to run in over the course of 1 hour. The mixture containing the crystals is then cooled to 0°-5° C. and stirred at this temperature for 1 hour. It is then filtered and the crystals are rinsed with 400 g of distilled water at 10° C. The crystals are dried in vacuo at 50° C. in a vacuum drying cabinet.

Yield: 73.0 g of phenylmaleimide, corresponding to 88.2% of theory, relative to aniline (theory = 83.67 g.) Melting point: 76°-78° C. N content (Kjehldal method): 94.15%. Free amine: < 0.2%.

EXAMPLE 10

45.0 g of 4,4'-diaminodiphenylsulphone (0.1812 mol) and 100.0 g of dimethylformamide are introduced into a flask equipped with a reflux condenser. The mixture is stirred at 25° C. until a solution results. This solution is warmed to 60° C. A solution of 37.1 g of maleic anhydride (0.378 mol) in 68.0 g of dimethylformamide is added dropwise to the above solution over the course of 1 hour at 60°-65° C. The reaction mixture is stirred for 1 hour at 60°-65° C. It is then cooled to 25° C. and 55.8 g of acetic anhydride (0.5465 mol), 3.57 g of calcium acetate (anhydrous; 0.0225 mol) and 5.49 g of triethylamine (0.0543 mol) are added in succession. The reaction mixture is warmed to 60°-65° C. and kept at this temperature for 2 hours, whilst stirring. A solution of medium viscosity results, which is allowed to cool to 30°-35° C. 1,000 g of distilled water are run in over the course of 1 hour. The mixture is then cooled to 0°-5° C. and stirred at this temperature for 1 hour. It is then filtered and the crystals are rinsed with 300 g of distilled water at 10° C. The crystals are dried in vacuo at 100° C. in a vacuum drying cabinet.

Yield: 71.6 g of N,N'-4,4'-diphenylsulphone-bismaleimide, corresponding to 96,7% of theory, relative to 4,4'-diaminodiphenylsulphone (theory = 74.01 g). Melting point: 154°-148° C. N content (Kjehldahl method): 84.25%. Free amine (by titration with sodium nitrite) < 0.3%. S content (determined gravimetrically via BaSO₄): 92.0% of the theoretical content.

EXAMPLE 11

35.0 g of 3,6-diaminodiphenylene oxide (0.1765 mol) and 200.0 g of dimethylformamide are initially introduced into a flask equipped with a reflux condenser. The mixture is warmed to 60° C. and the product is dissolved at this temperature. Thereafter a solution of 36.3 g of maleic anhydride (0.370 mol) in 70.0 g of dimethylformamide is added dropwise to this solution over the course of 1 hour at 60°-65° C. The reaction mixture is stirred for 1 hour at 60°-65° C. and then cooled to 25° C. 54.1 g of acetic anhydride (0.5299 mol), 3.62 g of calcium acetate (anhydrous; 0.0228 mol) and 5.35 g of triethylamine (0.0529 mol) are introduced in succession. The reaction mixture is warmed to 60°-65° C. and kept at this temperature for 2 hours, whilst stirring. A solution of medium viscosity results, which is allowed to cool to 30°-35° C. 1,300 g of distilled water are run in over the course of one hour. The mixture is then cooled to 0°-5° C. and kept at this temperature for 1 hour whilst stirring. The resulting crystals are then filtered off and rinsed with 300 g of distilled water at 10° C. The crystals are dried in vacuo at 100° C. in a vacuum drying cabinet.

Yield: 59.53 g of N,N-3,6-dimaleimide-diphenylene oxide, corresponding to 93.6% of theory, relative to 3,6-diaminodiphenylene oxide (theory = 63.61 g). Melting point: 179°-181° C. N content (Kjehldal method): 92.76%. Free amine (by titration with sodium nitrite): < 0.3%.

What I claim is:

1. An improved process for the manufacture of monomaleimides or polymaleimides by cyclising dehydration at temperatures between 40° and 100° C. of a member selected from the group consisting of
   (a) phenyl maleamic acid,
   (b) a polymaleamic acid of the general formula

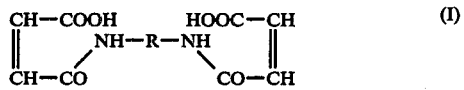

in which R denotes a radical of the formula

wherein R¹ represents one of the radicals —CH₂—,

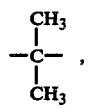

—SO₂— —SO—, —S—, —CO— and —O—,
   (c) a polymaleamic acid of the formula

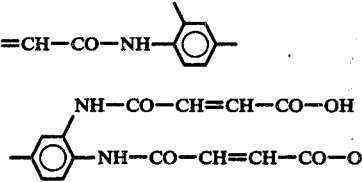

and
   (d) a polymaleamic acid of the formula

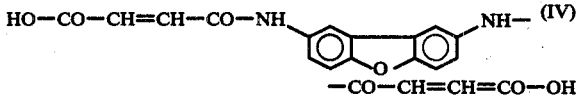

in the presence of acetic anhydride, a catalyst, and a member selected of the group consisting of trialkylamines and N,N-dialkylbenzylamines with 1 to 12 C atoms in each alkyl group and in the presence or absence of organic solvents, wherein the improvement comprises employing as catalyst a calcium, barium or strontium oxide, acetate or alcoholate in a concentration of 0.005 to 0.2 mol per mol of the monomaleamic or polymaleamic acid.

2. Process according to claim 1, characterised in that the catalyst is employed in a concentration of 0.01 to 0.1 mol per mol of the monomaleamic acid or polymaleamic acid.

3. Process according to claim 1, characterised in that a calcium, barium or strontium oxide is employed as the catalyst.

4. Process according to claim 1, characterised in that a calcium, barium or strontium acetate is employed as the catalyst.

5. Process according to claim 1, characterised in that a calcium compound or barium compound is employed as the catalyst.

6. Process according to claim 1, characterised in that a polymaleamic acid of the formula (I) in which R denotes a radical of the formula

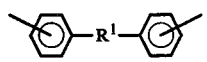 (II)

wherein $R^1$ represents one of the radicals —CH$_2$, $$-\underset{\underset{CH_3}{|}}{\overset{\overset{CH_3}{|}}{C}}-,$$

—SO$_2$—, —SO—, —S—, —CO— and —O—, is employed.

7. Process according to claim 6, characterised in that N,N'-4,4'-diphenylmethane-bis-maleamic acid or N,N'-4,4'-diphenylsulphone-bis-maleamic acid is employed as the polymaleamic acid of the formula (I).

8. Process according to claim 1, characterised in that the cyclising dehydration is carried out at temperatures between 40 and 60° C.

9. Process according to claim 1, characterised in that phenylmaleamic acid or polymaleamic acids are employed which have been manufactured by reaction of maleic anhydride with aniline or polyamines in the presence of organic solvents and in the presence of 0.005 to 0.2 mol of a catalyst per mol of the monoamine or polyamine.

10. Process according to claim 9, characterised in that phenylmaleamic acid or polymaleamic acids are employed which have been manufactured by reaction of maleic anhydride with aniline or polyamine in a ratio such that there are 0.8 to 1.2 mols of maleic anhydride per equivalent of amine.

11. Process according to claim 10, characterised in that phenylmaleamic acid or polymaleamic acids are employed which have been manufactured by reaction of maleic anhydride with aniline or monoamine or polyamine in a ratio such that there are 0.95 to 1.1 mols of maleic anhydride per equivalent of amine.

12. Process according to claim 1, characterised in that a polymaleamic acid of the formula

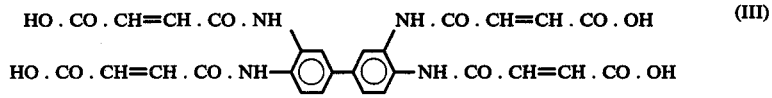 (III)

is employed.

13. Process according to claim 1, characterised in that phenylmaleamic acid is employed as the monomaleamic acid.

14. Process according to claim 1, characterised in that a polymaleamic acid of the formula

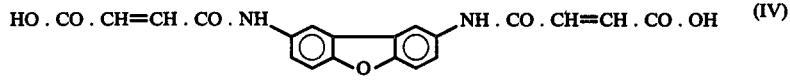 (IV)

is employed.

* * * * *